United States Patent [19]
Gorman

[11] Patent Number: 5,913,827
[45] Date of Patent: *Jun. 22, 1999

[54] PERSONAL MONITOR AND METHOD FOR MONITORING A BIOMEDICAL CONDITION IN THE PRESENCE OF INTERFERENCE

[76] Inventor: Peter Gregory Gorman, Lakeview Dr., Mahopac, N.Y. 10541

[*] Notice: This patent issued on a continued prosecution application filed under 37 CFR 1.53(d), and is subject to the twenty year patent term provisions of 35 U.S.C. 154(a)(2).

[21] Appl. No.: 08/684,302

[22] Filed: Jul. 18, 1996

Related U.S. Application Data

[63] Continuation of application No. 08/380,370, Jan. 30, 1995, Pat. No. 5,538,007, which is a continuation of application No. 08/065,564, May 21, 1993, Pat. No. 5,394,879, which is a continuation-in-part of application No. 08/033,826, Mar. 19, 1993, Pat. No. 5,400,797.

[51] Int. Cl.$^6$ ................................................. A61B 5/0402
[52] U.S. Cl. ........................................... 600/509; 128/903
[58] Field of Search ................................... 128/696, 903; 600/509

[56] References Cited

U.S. PATENT DOCUMENTS

| | | | |
|---|---|---|---|
| 3,218,638 | 11/1965 | Honig | 128/903 |
| 3,846,704 | 11/1974 | Bessette | 325/66 |
| 3,943,918 | 3/1976 | Lewis | 128/903 |
| 3,972,320 | 8/1976 | Kalman | 128/2.1 |
| 4,958,645 | 9/1990 | Cadell et al. | 128/903 |
| 5,157,604 | 10/1992 | Axford et al. | 128/903 |

FOREIGN PATENT DOCUMENTS

| | | |
|---|---|---|
| A1 296068 | 7/1986 | Canada . |
| 0 212 278 | 7/1986 | European Pat. Off. . |
| 2 187 554 | 9/1987 | United Kingdom . |
| WO 93/01574 | 1/1993 | WIPO . |

OTHER PUBLICATIONS

Jerry J. Cupal et al, Biotelemetry X, pp. 39–50, Amlaner, Fayetteville, AR, Jul. 31–Aug. 5, 1988.
F.W. Anderka, Biotelemetry VIII, pp. 405–408 (1984).
B. Puers et al, Sensors and Actuators A, 37, 38, pp. 260–267 (1993).
F.A. Spelman et al, IEEE Trans. On Biomedical Engineering, vol. 38, No. 12, pp. 1175–1185, Dec. 1991.
P. Wouters et al, Abstract of Paper in ESSCIRC '91 Conference.
J.J. Cupal et al, IEEE Annual Conference of the Engineering In Medicine and Biology Society, 1987.

*Primary Examiner*—William E. Kamm

[57] ABSTRACT

A personal monitor for monitoring a biomedical condition, such as a heart rate. A sensor provides a signal related to the biomedical condition and the signal is encoded for repeated wireless transmission to a receiver. An encoded identification signal is also repeatedly sent to the receiver to identify the transmitter to the receiver in order to prevent the adverse effects of interference which occurs if signals other than those from the transmitter are received. The monitor detects deviations (errors) from an expected pattern and recovers from these deviations (error correction) to display an accurate value of the biomedical condition. If too many errors are present due to interference, faulty transmission and/or reception, etc., the frequency over which wireless transmission occurs can be changed. In one embodiment, the value of the biomedical condition is wirelessly sent to the receiver. In another embodiment, the value of the biomedical condition is determined in the receiver based on the encoded signal that is received. The receiver rejects all signals that are not from the transmitter.

45 Claims, 6 Drawing Sheets

FIG. 1
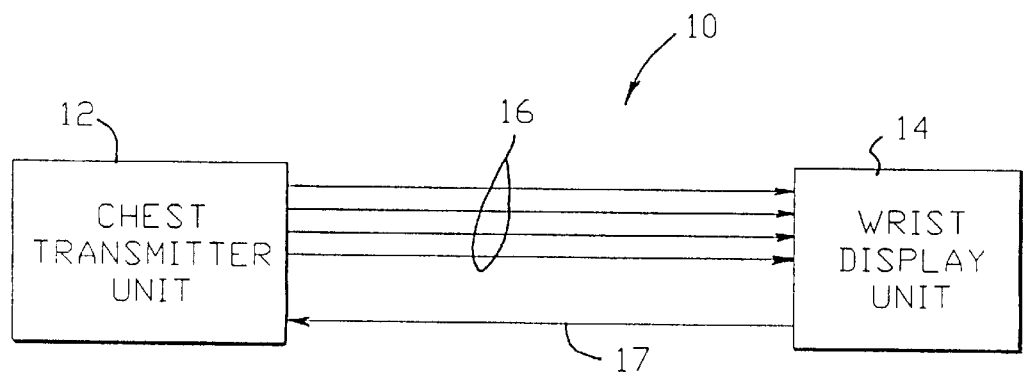
FIG. 2
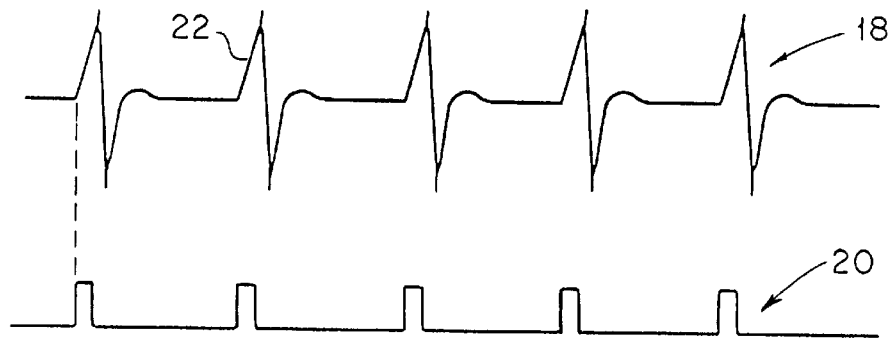
FIG. 3A
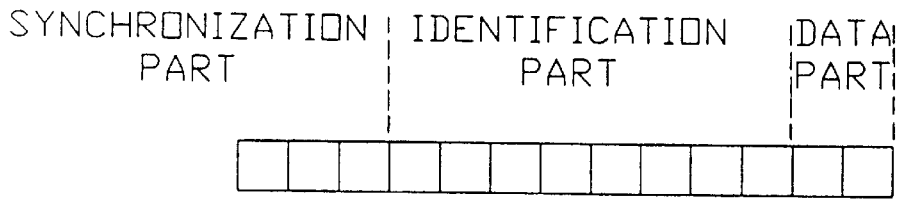
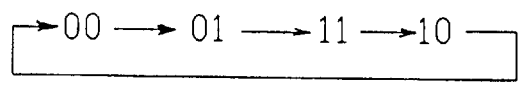
FIG. 3B

TRANSMITTER UNIT

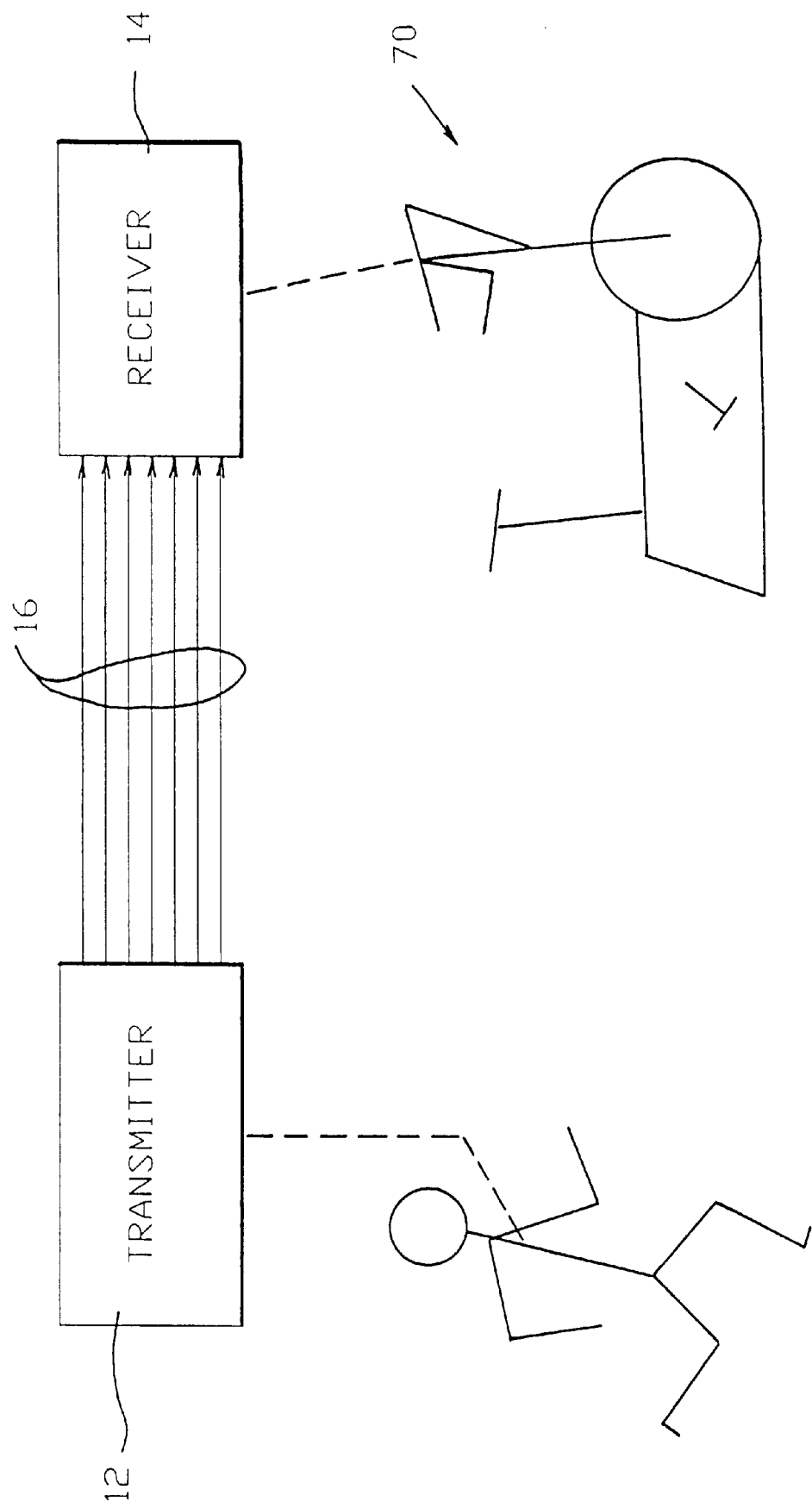

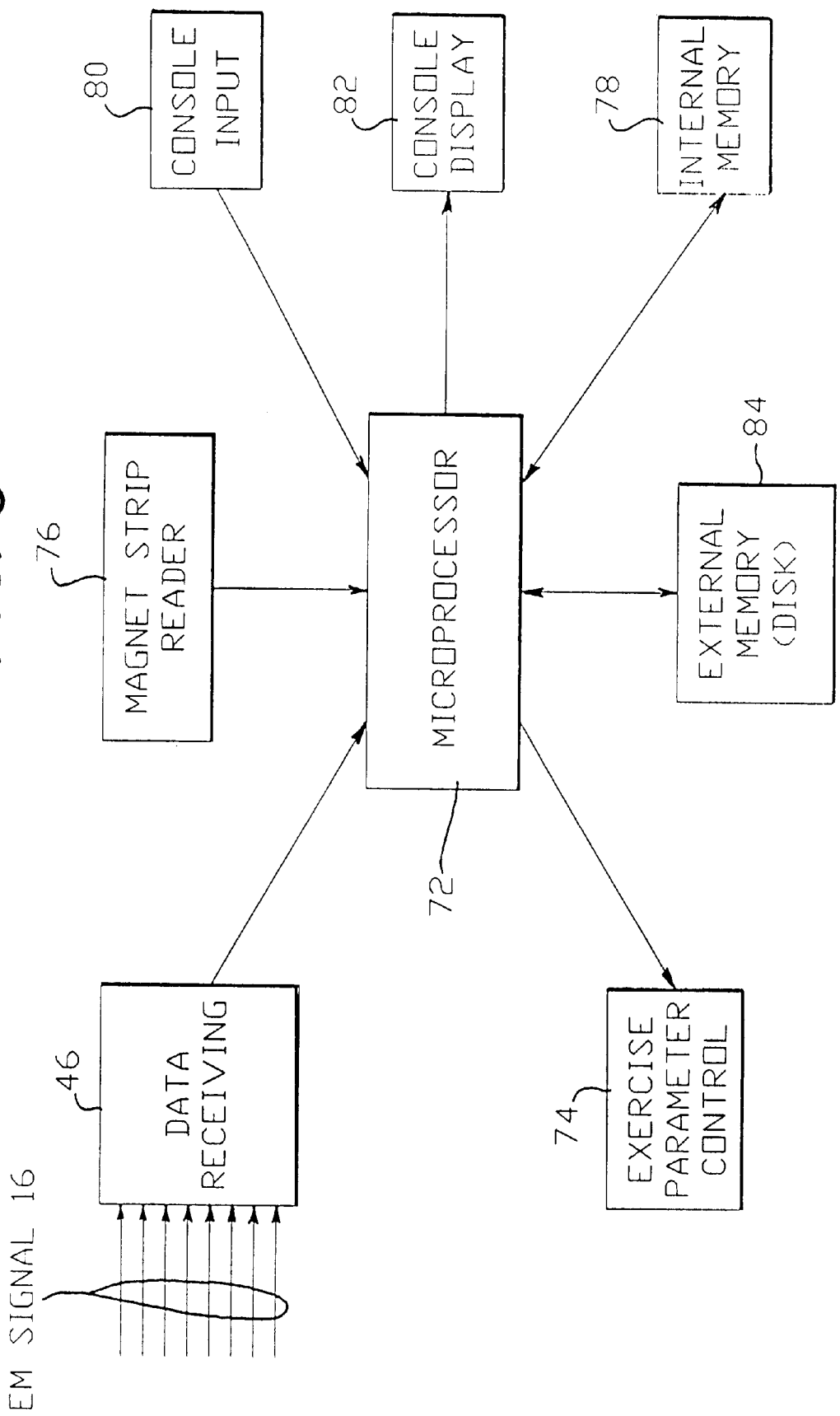

PERSONAL MONITOR AND METHOD FOR MONITORING A BIOMEDICAL CONDITION IN THE PRESENCE OF INTERFERENCE

CROSS REFERENCE TO RELATED APPLICATIONS

This application is a continuation of application Ser. No. 08/380,370 filed Jan. 30, 1995 (now U.S. Pat. No. 5,538,007) which is a continuation of application Ser. No. 08/065,564 filed May 21, 1993 (now U.S. Pat. No. 5,394,879), which is a continuation-in-part of application 033,826 filed Mar. 19, 1993 (now U.S. Pat. No. 5,400,797).

FIELD OF THE INVENTION

This invention relates to controlled exercise using an apparatus for monitoring a physical condition or body response such as heart rate, and more particularly to controlled exercise equipment in which errors due to interfering sources are minimized or eliminated and in which improved accuracy results due to error detection and correction in the pattern representing the body response.

BACKGROUND ART

For many applications, it is necessary to measure and display a person's body response, such as his or her heartbeat. In particular, in exercise and fitness training, it is often the situation that a person wishes to measure his or her heartbeat in order to achieve the maximum benefits of the exercise without the danger of increasing the heartbeat to a rate where adverse effects could occur. Of course, such measurements are also useful for many health applications such as biofeedback and exercise programs where the participants only mildly exercise and do not approach greatly elevated heart rates. Over the years, various types of equipment have been marketed for the measurement of heart rate, such instruments being popular in a wide variety of applications extending from all forms of exercise to biofeedback. Continuous accurate heart measurement is an important part of all aerobic exercise and rehabilitation programs and for this reason many types of apparatus have been commercially available for personal use by individuals and in fitness clubs, etc. Some of this equipment includes heart rate monitors that are used to control the intensity of the workout based on the user's measured heart rate. As will be discussed later, the problem of providing a good monitor necessarily affects the quality of an exercise program that is responsive to a measured heart rate.

Some of the most popular heartbeat monitor designs use wireless data transmission from a sensor-transmitter unit to a display unit. This type of design allows optimal and flexible positioning of both units while not limiting a person's freedom of movement. Unfortunately, the increasing popularity of heart measurement, and therefore the use of these heart monitors, has demonstrated the limitations of currently available designs. An example is the recurring interference effects brought about when a person wearing a heart monitor is in close proximity to another person wearing another heart monitor. These people run the risk that their individual monitor readings are influenced by the monitor worn by the other person. Further, it is equally frustrating for a person wearing a heart monitor to find that electromagnetic equipment of all types, such as exercise equipment, power lines etc. will crate electromagnetic fields that interfere with the successful transmission of his or her heartbeat, thereby causing an erratic display which is uncorrectable without moving away from the interfering exercise equipment, power lines, etc.

Various types of wireless measuring methods have bene proposed. Some of these are based on radio waves while others use a magnetic proximity field. Most of these prior techniques transmit an analog ECG signal of a person. However, as noted, these prior techniques and apparatus are not simultaneously usable by several persons in close proximity to one another or by persons who are using such apparatus in close proximity to electrical or electronic equipment. In such cases, the reliability of transmission of heartbeat is significantly reduced with the result that a continuous and accurate monitoring of the heartbeat is no longer possible. As is readily appreciated, this lack of reliability is a problem for anyone using the monitor and is especially disconcerting to a person who is exercising to a level where his or her heartbeat is close to the maximum desired for that person.

Examples of some prior art monitors include U.S. Pat. Nos. 4,625,733; 4,425,921; 3,212,496; and 3,939,388. The first of these describes a heartbeat monitor using a magnetic proximity field as a basis for analog wireless transmission, where a particular arrangement of magnetic coils is used in the transmitter and the receiver units.

U.S. Pat. No. 4,425,921 describes a portable heartbeat monitor which can be used to check either pulse rate or heart rate using separate sensors for detecting heartbeat and pulse beat. The apparatus shares a common indicator for displaying the heartbeat rate or pulse beat rate depending upon a switch means for connecting either of the sensors to a microcomputer. Analog signals are used in this monitor, which does not use wireless transmission between a transmitter and receiver.

U.S. Pat. No. 3,212,496 describes an apparatus for simultaneously measuring ECG, respiration rate, and respiration volume. A pair of electrodes on or in a person's body have current passed therebetween and sense an impedance change and a heartbeat voltage. A frequency modulated signal can then be telemetered to a receiving and display unit.

U.S. Pat. No. 3,949,388 describes a portable apparatus that can be used for analog biomedical telemetry, and is particularly adapted for use in a hospital where each sensor-transmitter unit is used on a single patient and will not normally be used on another patient. The transmitter is designed to produce a very narrow frequency spectrum where a steady pulse rate accurately represents the measured temperature of the patient. In order to avoid interference from adjacent units, the receiver unit is located within only a few feet of the transmitting unit. Further, a very low power continuously sending transmitting unit is used so that only the closest receiver will detect the analog signal. This avoids the possibility that the receiver will pick up signals from another transmitter. Thus, the selectivity of the receiver is based on its close proximity to the associated transmitter unit, not on any circuitry which would prevent interference by a transmitter broadcasting a high power signal, even though such interfering transmitter may be far away. Further, the frequency range intended for operation is selected to be very narrow. As noted in this patent, frequency sweeping can occur due to saturation of a transistor in the oscillator circuit. In order to prevent this undesirable frequency sweeping, an isolating impedance is used in the circuit design to prevent feedback current of the type which causes the transistor saturation.

U.S. Pat. No. 5,157,604 describes a hospital monitoring system in which many patient transmitter units are coupled to a central station. Wireless transmission of a signal including an identifier and heartbeat data occurs from each patient unit to the central station. Each patient unit transmits on its own frequency so there will be no interference between the patient units. The responses of the patient units are time multiplexed, since these units respond to the central station only in response to the receipt of a timing signal from the central station. Error detection and correction of an incorrect heartbeat due to faulty transmission is not mentioned.

In the prior art monitors for measuring and displaying heartbeat, it is usually not possible to provide a technique and apparatus for determining if the received signal in the display unit is from the properly associated transmitter unit or is instead from another transmitter unit. Further, if there are errors occurring in the data representing the heartbeat, such as missing portions of the signal due to interference from outside sources, the display in these prior monitors will either indicate a wrong value, not indicate heartbeat, or maintain the previous reading without making the user aware of the problem. In these prior art monitors, there is no way to account for transient errors in heartbeat which are momentarily caused but which do not necessarily render inaccurate the later readings of heartbeat. If these prior art monitors are used to control exercise equipment, there is a problem due to interference from the motors in the equipment and also from other monitors on equipment that is closely located to the user's exercise equipment.

It is therefore a primary object of the present invention to provide an improved technique and apparatus for monitoring and displaying a biomedical function (body response) such as heartbeat, wherein the above-described problems are addressed and corrected and to provide exercise equipment using this improved apparatus.

It is another object of the present invention to provide exercise equipment using an improved personal use heartbeat monitor which automatically rejects interfering signals from sensor-transmitter units other than the one with which the display unit is properly associated.

It is another object of the present invention to provide a heartbeat monitor in which the presence of transient errors in the signal representing the heartbeat does not render inaccurate the heartbeat displayed to the person wearing the monitor, where this monitor is used to control exercise equipment in accordance with the person's instantaneous heart rate.

It is another object of this invention to provide a wireless heartbeat monitor which can be easily worn by a person engaged in all forms of physical exercise, and which will nonetheless provide accurate measurement of the person's heartbeat even in the presence of the other heartbeat monitors and/or electrical or electronic equipment in which components of the monitor are located.

It is another object of the present invention to provide exercise equipment in which a part of a person's ECG signal is digitally encoded for wireless transmission to a receiver-display unit located in the exercise equipment, where the coding allows a receiver-display unit to identify the encoded digital signal as having been sent from a particular sensor-transmitter unit.

It is another object of the present invention to provide exercise equipment using a heartbeat monitor which will automatically change the frequency range over which signals representing the heartbeat are wirelessly sent from a sensor-transmitter unit to a receiver-display unit, the transmission frequency being changed in response to the occurrence of errors in the received signal.

It is a further object of this invention to provide a technique and apparatus for monitoring heartbeat where the monitor is used in exercise equipment without adversely affecting the accuracy of the data displayed to the person using the monitor.

It is another object of this invention to provide improved exercise equipment for isolating monitor signals relating to a biological function, such as heartbeat, wherein the monitored signals are digitally encoded to provide user identifiers that are wirelessly transmitted.

It is a still further object of this invention to provide automatic transmission error detection and correction in a wireless biological response monitoring system used to control exercise equipment in accordance with a user's biological response.

BRIEF SUMMARY OF THE INVENTION

This invention broadly relates to exercise equipment that uses an improved technique and monitor for measuring and displaying, preferably on a continuous basis, a physical condition or biomedical response, such as a heartbeat rate. The monitor includes a transmitter unit for producing an encoded digital signal representing the biomedical response and for wirelessly transmitting the encoded digital signal to a receiver unit for display of the measured biomedical response. The monitor also includes a detection means for detecting errors in the received encoded digital signal, and correction means for automatically changing the transmitter unit and the receiver unit to provide accurate wireless transmission therebetween of the measured biomedical response. In a preferred embodiment this monitor includes unique identification between a transmitter and an associated receiver.

This monitor is particularly suitable for personal use such as would occur in a home or office or even in a gym or fitness center where it can be a part of exercise equipment. In one embodiment, the transmitter unit is adapted to be worn and would be battery operated while the receiver unit can be part of exercise equipment and can be used to control a workout in response to a measured biological response. As long as the receiver is within the transmission distance from the transmitter, it will receive the wirelessly transmitted signal. In one aspect of this invention the monitor measures a person's heartbeat and displays an indication of the monitored heartbeat. In this embodiment, the apparatus is comprised of a sensor-transmitter unit (chest unit) adapted to be worn in contact with a person's chest and having electrodes which receive the person's ECG signal. This signal is amplified and digitally encoded to contain an identification portion and a data portion. This encoded signal is transmitted in a wireless manner to a receiver-display unit (wrist unit), where the receiver-display unit contains a display for displaying the person's heartbeat. While the receiver-display portion of the monitor can be adapted to be work, for exp. on a person's wrist, this unit need not be worn and could be located elsewhere, for example on exercise equipment. In the invention of this continuation-in-part application the receiver-display unit is used to control the exercise equipment in response to a continuous monitoring of the exercising person's biological response (heart rate, etc.). Further, while chest electrodes generally provide the best ECG signals, the transmitter unit could be placed elsewhere, such as on a person's wrist.

Because the person's ECG signal is digitized and encoded, two purposes can be achieved. The first is that an identification is provided which is different for each heart monitor. That is, after the receiver-display unit receives the transmitted encoded signal, it checks this signal to see if it contains the proper identification code. If this comparison fails, the incoming signal to this unit is not accepted because it is not from the proper chest unit. However, if the identification compares with the reference identification in the receiver unit, the incoming signal will be accepted. This prevents two heart monitors working in close proximity to each other and transmitting on the same frequency from receiving and displaying signal from the wrong person.

The second purpose of the digital encoding is to provide transmission error detection and correction of the heartbeat data. In practice, it is possible that a valid signal may be rejected by the receiver-display unit due to an outside noise source. The data portion of the transmitted signal is therefore encoded into a particular bit sequence. When the incoming data bit sequence is checked against a reference data bit sequence in the receiver-display unit, errors in the received signal can be detected. The receiver unit can be set so that infrequently occurring errors (such as transient errors) will be corrected but not result in a change of the transmitting and receiving units. On the other hand, if too many errors are present, the receiver unit will notice it and provide a frequency change signal to change the transmission frequency in the chest unit and also to change the receiving frequency in the receiving unit. In a preferred embodiment the power of the frequency change signal is also increased to ensure that the frequency change is made. While the receiving unit will automatically cause a change in frequency if persistent errors occur, the user can also change the transmission and reception frequency if it is anticipated that a problem may occur. This feature of a change in transmission and receiver frequency also allows the use of multiple units in close proximity to one another without reciprocal disturbances.

The chest unit generally contains an input sensor means for receiving the ECG signal, amplifying means, comparator means for producing a digital pulse train corresponding to the analog ECG pulses, encoder means for encoding the digital pulse train into coded signals having bits corresponding to an identification portion and further bits corresponding to a data portion of said encoded signal, and means to receive a frequency change signal from the wrist (receiving) unit for changing the transmitting frequency of the chest unit. This latter means includes a receiver for receiving via wireless transmission the frequency change signal from the receiving unit when the transmission frequency is to be changed and a signal evaluator for reading the identification code in the frequency change signal to determine that it is from the associated receiving unit and for providing a signal to the transmitter means for changing the transmission frequency for the outgoing signals form the chest unit. Part of the identification signal may serve for synchronization of a clock signal in the receiving and transmitting units.

The receiving unit broadly includes a receiver for receiving output signals from the chest unit and a signal evaluator for separating the identification portion and the data portion of the incoming encoded signal and for determining if the incoming signal is from the associated chest unit. The signal evaluator also checks the data portion of the incoming signal to determine if it has the proper data pattern for the associated chest unit. The signal evaluator provides an output to a memory means for storing heartbeat data and also provides an output that is sent to a display, for displaying the heartbeat rate. The signal evaluator further provides an output that is sent to a transmitter means located in the receiving unit if the signal evaluator determines that the frequency of errors in the data portion of the incoming signal is beyond a given bound, that is, if the bit patterns indicate that the errors are not merely transient but are sufficiently repetitive as to provide potentially inaccurate monitoring of person's heartbeat. The output of the transmitter means in the receiving unit is sent in a wireless manner to the receiver in the chest unit. At the same time, the signal evaluator also provides a signal to the receiver in the receiving unit to change its reception frequency to match the new transmission frequency in the chest unit. The receiving unit also contains an input terminal by which the user can directly initiate a change in transmitter/receiver frequency, or can block an automatic change of frequency in the chest and receiving units. For example, the user may sense that the external condition which is causing an error in the received encoded signal will soon cease so that it is not necessary to change frequency. Another situation where a user may want to prevent a frequency change is where there are multiple users in close proximity. Rather than have everyone's monitor change frequency, some monitors can be held at fixed frequencies while other monitors change frequency.

This design will overcome most of the limitations of the currently available wireless heart monitors. Additionally, it will compensate for minor errors and enable the user to avoid certain error sources by purposely changing the transmission frequency. Of course, the user can allow the monitor to automatically change frequencies. Since the range of the human heart rate is fairly restricted, this design allows the detection of uncorrectable errors by taking into account the elapsed time between two successful data transmissions. Since it is highly improbable that the wrist unit will receive the correct identification pattern from a source other than the associated chest unit, the user can have a very high level of confidence in the accuracy of the displayed heart rate. This is accomplished even though the chest and receiving units are separate from one another and communication therebetween is via wireless transmission.

The invention uses the improved monitor to control exercise equipment in response to a measured biomedical function such as heart rate. The receiving unit is located on the exercise equipment and provides a control signal to change (increase or decrease) or maintain the resistance offered to the user by the exercise equipment. This resistance is changed in accordance with the measured heart rate (for exp.) in a continuous manner to provide an exercise workout including warm-up, cool-down and sustained aerobic exercise.

Memory means and a microprocessor are used to maintain an up-to-date profile of the exercising person and to continuously regulate the resistance of the equipment in accordance with the user's instantaneous heart rate. Identification means allows the user to identify himself or herself to the exercise equipment in order to have the equipment access the proper exercise profile from memory. Additional memory is provided to allow the user to enter a different exercise profile if it is not desired to use the exercise profile already stored in memory. An input control to the microprocessor allows the user to override any profile control that the microprocessor would usually select.

The invention is most useful in the case of personal use equipment which allows the user to have complete mobility while undergoing heartbeat monitoring. The various components of the chest and wrist units are easily provided by known microelectronic integrated circuit chips that can be packaged together in small volume and battery operated. The major use of this monitor will be for continuous display during personal activities by an individual, including exercise, biofeedback, and general health monitoring. In these activities wireless transmission will be over a relatively short range, particularly if both the transmitter and receiver units are worn or if the receiving unit is located in the exercise equipment.

These and other objects, features, and advantages will be apparent from the following more particular description of the preferred embodiments.

BRIEF DESCRIPTION OF THE DRAWINGS

FIG. 1 is a schematic illustration of the heart rate monitor of the present invention, showing the chest unit (transmitting unit) and the wrist unit (display) which receives the signal from the chest unit via a wireless transmission and displays the heartbeat of the person being monitored.

FIG. 2 shows a typical ECG signal and the train of digital pulses representing each of the analog pulses in the ECG signal.

FIG. 3A shows a typical format of the encoded digital signal wirelessly transmitted from the chest unit to the wrist unit, this digital signal consisting of a synchronization part, an identification part unique to this particular chest monitor and a data part unique to the person's heartbeat.

FIG. 3B represents a sequence of bits corresponding to the data part of the outgoing digital signal from the chest unit (FIG. 1) where each data part is represented as a two-bit binary code in this example.

FIG. 7 schematically illustrates the use of this invention monitor to control exercise equipment in accordance with a user's heart rate.

FIG. 8 shows the various components of the receiver-controller unit in the exercise equipment depicted in FIG. 7.

DETAILED DESCRIPTION OF THE PREFERRED EMBODIMENTS

Figure 4:
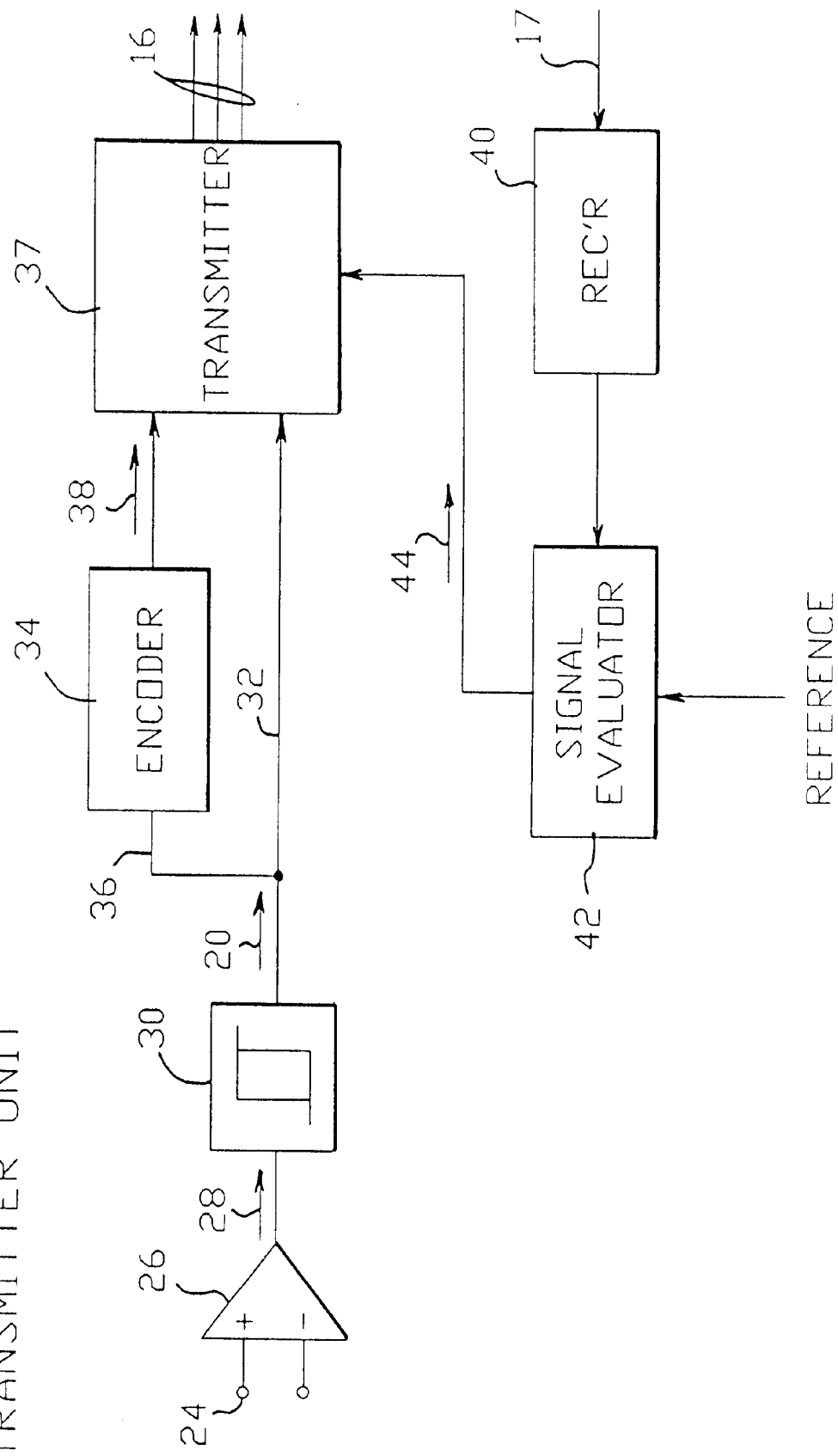
FIG. 4 is a schematic illustration of the chest unit in more detail, showing the various components of this unit.

In practice of this invention will be represented by the example of a heartbeat monitor, where it is desired to accurately measure heartbeat and to provide a technique which eliminates many of the errors found in the use of presently available wireless heartbeat monitors, particularly those of the portable type adapted to be used by people undergoing exercise, biofeedback etc. Such problems generally relate to interference effects that can occur if two wireless heartbeat monitors are operating in close proximity to one another, noise attributable to sources other than another heart monitor, confusion between received signals wherein the heartbeat being displayed may not be that of the person being monitored and situations where the user would be unaware that the displayed heartbeat is inaccurate.

FIG. 1 schematically represents the heartbeat monitor 10, which is comprised of a chest unit 12 (transmitting unit) and a complementary wrist unit 14 (receiving or display unit). Wireless transmission over a plurality of frequency ranges can occur from chest unit 12 to wrist unit 14, as represented by the arrows 16. Wireless transmission from the wrist unit 14 to the chest unit 12 is used to correct transmission errors but usually over only a signal frequency as represented by the single arrow 17. As will be described later, wireless transmission from the display unit 14 to the chest unit 12 will occur when it is desired to change the transmission frequency from the chest unit. This can be done either automatically or on command by the user. In practice, the transmitter of the chest unit is frequency matched to the receiver in the wrist unit so that an encoded digital signal wirelessly transmitted from the chest unit 12 will be correctly received by the wrist unit 14.

FIG. 2 illustrates a typical ECG signal 18 from a person being monitored, and the digital pulse train 20 corresponding to the ECG signal. Each digital pulse corresponds to the onset of a positive slope portion 22 of the analog pulses forming the ECG signal train 18. As an alternative, each digital pulse can correspond to another portion of the analog pulses, such as the peak of each pulse. In the present invention, the ECG signal is digitized prior to wireless transmission from the chest unit 12 to the wrist unit 14. The purpose of this apparatus is to monitor heartbeat and therefore it is sufficient to transform the ECG signal into a digital pulse train. The particular characteristics relating to a person's ECG signal are not of importance in the present invention.

Prior to the transmission of a digital signal from chest unit 12 to wrist unit 14, the digital signal is given a specific binary identification sequence.

Further, the individual digital pulses in the pulse train 20 are each encoded into m bits. A sequence of digital pulses will therefore result in a sequence of these m bit signals. This sequence is predetermined and is known to the wrist unit 14. A certain bit sequence can precede the identification portion with the encoded digital signal to facilitate synchronization of the transmitter and receiver. FIG. 3A shows a typical format of the encoded digital signal transmitted from the chest unit 12 to the wrist unit 14 where the signal is comprised of a 3 bit synchronization part, an 8 bit identification part and a two bit data part. FIG. 3B shows a sequence of four digital pulses represented by a code having two bits per pulse, i.e., m=2. In this sequence, the first encoded group 00 represents the first digital pulse, the second encoded group 01 represents the second digital pulse, the third encoded group 11 represents the third digital pulse, and the next encoded group 10 represents the fourth digital pulse. This pattern, and its order, will be used each time the ECG signal is sampled and encoded. The pattern and its order will be changed if m is changed.

In operation, it is possible that a transmission error can occur. Sometimes these errors are only transient, in which case the last display reading will be maintained. It can also be the situation that the errors continue to occur due to interference from some outside source (such as an adjacent heartbeat monitor) where the errors are, for example, missing bits during repeated transmissions. Since the wrist unit 14 knows the predetermined code for the data portion of the signal, the mission of up to $2^m-1$ continuous signals will be immediately noticed and the missing signals can be accounted for. If too many signals ($>2^m-1$) are missing and therefore the interference is not a transient one, the frequency of the transmitter and receiver will be changed automatically. This can also be done on demand by the user. Thus, encoding of the digital pulse train 20 to include an identification part and a data part enables the receiving unit to accept only those signals sent from the associated chest unit and to detect and correct errors in the data part corresponding to the person's heartbeat. Details of how this occurs will be explained with respect to the apparatus of FIG. 4 (chest unit and FIG. 5 (wrist unit).

Heartbeat Monitor Technique

This section will describe in general terms the technique of the present invention in which heartbeat monitoring is achieved in an advantageous manner. In a first step, a person's ECG signal is detected and then sufficiently amplified. This amplified signal is transformed into a digital pulse signal which can be used to initiate the wireless transmission of an encoded digital signal from the chest unit 12 to the wrist unit 14. The digital signal being transmitted includes an identification part and a data part as illustrated in FIG. 3A. The transmitted encoded data signal is received by a complementary receiver in wrist unit 14 and transformed therein back into the encoded digital signal. The resulting digital signal is separated into its identification part and its data part. Wrist unit 14 verifies the identification sequence to determine that the received signal is from the proper chest unit. If not, the signal is not accepted. If the identification step is satisfied, the data portion of the received signal is then checked to see whether it has the expected value. If the expected value is present in the received signal, then the display portion of the wrist unit is updated. Some or all of the data can also be stored in a memory contained in the wrist unit. As an option, the data can be first sent to the memory prior to being displayed.

The data portion of the transmitted encoded signal can represent a full heartbeat rate, or just a portion of it. For example, the number of ECG pulses in a 3-second interval can be represented. If this number is multiplied by 20, the approximate heartbeat rate in beats per minute will be known. This calculation can be done in the receiver unit or in the transmitter unit if the full heartbeat rate is to be transmitted to the receiver.

If the full heartbeat rate is transmitted, then less transmissions will be needed. In turn, this means that there will be less likelihood of interference from other sources and less power will be consumed. Of course, the number of transmissions in a given time from the transmitter to the receiver can be determined as a design parameter in accordance with considerations such as power, likelihood of interference, clocking requirements, etc. Various coding schemes are well known for selecting the number of ECG pulses to sample and the sampling repetition rate. In the practice of this invention, any of these known coding schemes, or a different one, can be chosen.

If the sequence of bits forming the data portion of the received signal is not maintained in the expected sequence, an error has occurred and the number of missing digital pulses is determined. These missing digital pulses are assumed to be evenly distributed in a corresponding time range and the display will be updated and/or the data will be stored in memory together with some annotation about the error.

In this embodiment, the occurrence of a certain number of errors ($>2^m-1$) within a given time frame means that the indicated heart beat rate will be unreliable. This will result in an automatically generated request for a frequency switch that is initiated in the wrist unit 14. This request for a change in transmission frequency can be blocked by the user or can be initiated on demand by the user. For example, the user may see that he or she will be in the presence of others using heartbeat monitor devices or maybe near exercise or other types of equipment which would interfere with the signals being transmitted form the chest unit. Knowing that such an interference may occur and may extend for a period of time, the user may wish to change the transmission frequency in order to avoid problems. Alternatively the user may recognize that any interference will be only transient, and therefore may wish to block a frequency change. In actual use, most persons would allow the monitor to automatically adjust. The amount of errors that will trigger a frequency change is a parameter that can be varied, according to the logic incorporated in the monitor.

If a change in transmission frequency is needed, a digital signal (frequency change signal) will be sent via wireless transmission from the wrist unit to the chest unit. This digital signal can include an identification part and a data part which specifies the new transmission frequency. The identification part of this digital signal allows the chest unit to know that the frequency change signal has been sent from the associated wrist unit and is therefore a correct command to change frequency. At the same time, the wrist unit changes the frequency of the receiver in this unit to match the new transmitter frequency of the chest unit 12. The transmission path from the wrist unit 14 to the chest unit 12, commanding a new transmission frequency, is not often used. However, once it is used the probability of a correct transmission must be high. For these reasons, it is preferable that there be only one possible transmission frequency for this path and that this transmission frequency be different from the frequencies used on the main transmission path, i.e., the transmission frequencies normally used to transmit the encoded digital signals form the chest unit to the wrist unit 14. As a further measure to increase the reliability of the second transmission path from the wrist unit 14 to the chest unit 12, the power of the frequency change signal from the wrist unit to the chest unit is higher than the power normally used for the transmission of encoded digital signals from the chest unit 12 to the wrist unit 14. This ensures that the necessary frequency change in the main transmission path will be made.

The following description will detail the components comprising the chest unit 12 and the wrist unit 14, which together comprise the heartbeat monitor 10.

Chest Unit (FIG. 4)

FIG. 4 shows the various components of chest unit 12 which are used to detect an ECG signal, amplify that signal and digitize it, encode it into an identification portion and a data portion, and then to wirelessly transmit it to wrist unit 14. The chest unit also includes means for receiving a frequency change signal from the wrist unit that will trigger a change in transmission frequency of the outgoing signals.

In more detail, chest unit 12 is typically carried on the breast of the target person such that this person's ECG signal 18 can be received by the input electrode terminals 24. These terminals 24 can be a part of the chest unit or the chest unit can be designed so that any sensor for detecting a biomedical response can be plugged into it. The ECG signal 18 is then amplified in a differential amplifier 26, producing the amplified signal represented by arrow 28. Amplified signal 28 is transformed into a digital pulse train 20 (FIG. 2) in the comparator 30, which has hysteresis. This hysteresis feature prevents the generation of more than one digital pulse from one heartbeat, due to outside disturbances of any type. The correlation between the ECG signal 18 and the digital pulse signal 20 was described with respect to FIG. 2.

The digital pulse signal 20 is sent directly to the transmitter 37 via line 32, and is also sent to an encoder means 34 via interconnection line 36. The rising flank of a digital pulse will trigger transmitting means 37 to wirelessly transmit an encoded electromagnetic signal 16 to a receiving means in the wrist unit 14. The rising flank of a digital pulse also triggers encoder 34 to provide the synchronization part, the identification part and the data part of the encoded digital signal represented by arrow 38 which is transmitted by the transmitting means 37. The digital pulse on line 32 is used only as a clock or timing pulse. Line 32 can be eliminated in an alternative design wherein clocking is internal in transmitter 37 or is provided by a portion of the encoded signal from encoder 34.

Encoded digital signal 38 is shown in FIG. 3A, while a sequence of signals corresponding to the encoded data portion is shown in FIG. 3B. Every digital pulse in pulse train 20 (FIG. 2) results in advancing one step in the cycle of the encoded data signals. Therefore, FIG. 3B illustrates a pulse sequence corresponding to four digital pulses in the pulse train 20. Only a small and predetermined number of encoded signals must be transmitted by transmitting means 37.

Chest unit 12 also contains a receiver 40 and a comparator 42, termed a signal evaluator. Units 40 and 42 are used to receive a frequency change signal from wrist unit 14 indicating that a transmission frequency change is required, and to thereby provide a signal to the transmitter 37 to achieve this. In more detail, if errors beyond a given bound are noted in the data portion of the incoming digital signals in the wrist unit 14, a transmitted frequency change signal 17 will be wirelessly sent to chest unit 12 and is received by the receiver 40. This received signal contains the binary identification pattern unique to this heartbeat monitor and a data portion which will trigger a change in frequency. In this embodiment, chest unit 12 need not be equipped with error detection and correction means. It is only necessary that the data portion of the frequency change signal indicate that a new transmission frequency is desired. The data portion can also specify this new frequency or logic in signal evaluator 42 can specify the new frequency range over which the encoded digital signals will be sent.

The frequency change signal is sent to the comparator 42 (signal evaluator) which compares the coded identification pattern in the received digital signal with the coded identification pattern for this heartbeat monitor 10. As noted, this identification pattern is unique to this heartbeat monitor. If the comparison shows that the identification portion of the incoming signal matches that for this heartbeat monitor, comparator 42 will determine the new transmission frequency from the data portion of the received signal and will generate a digital frequency select signal 44 that is sent to the transmitter 37. As will be explained later, a signal evaluator in the wrist unit will provide a corresponding signal to the receiver therein in order that the reception and transmission frequencies will be matched.

Figure 5:
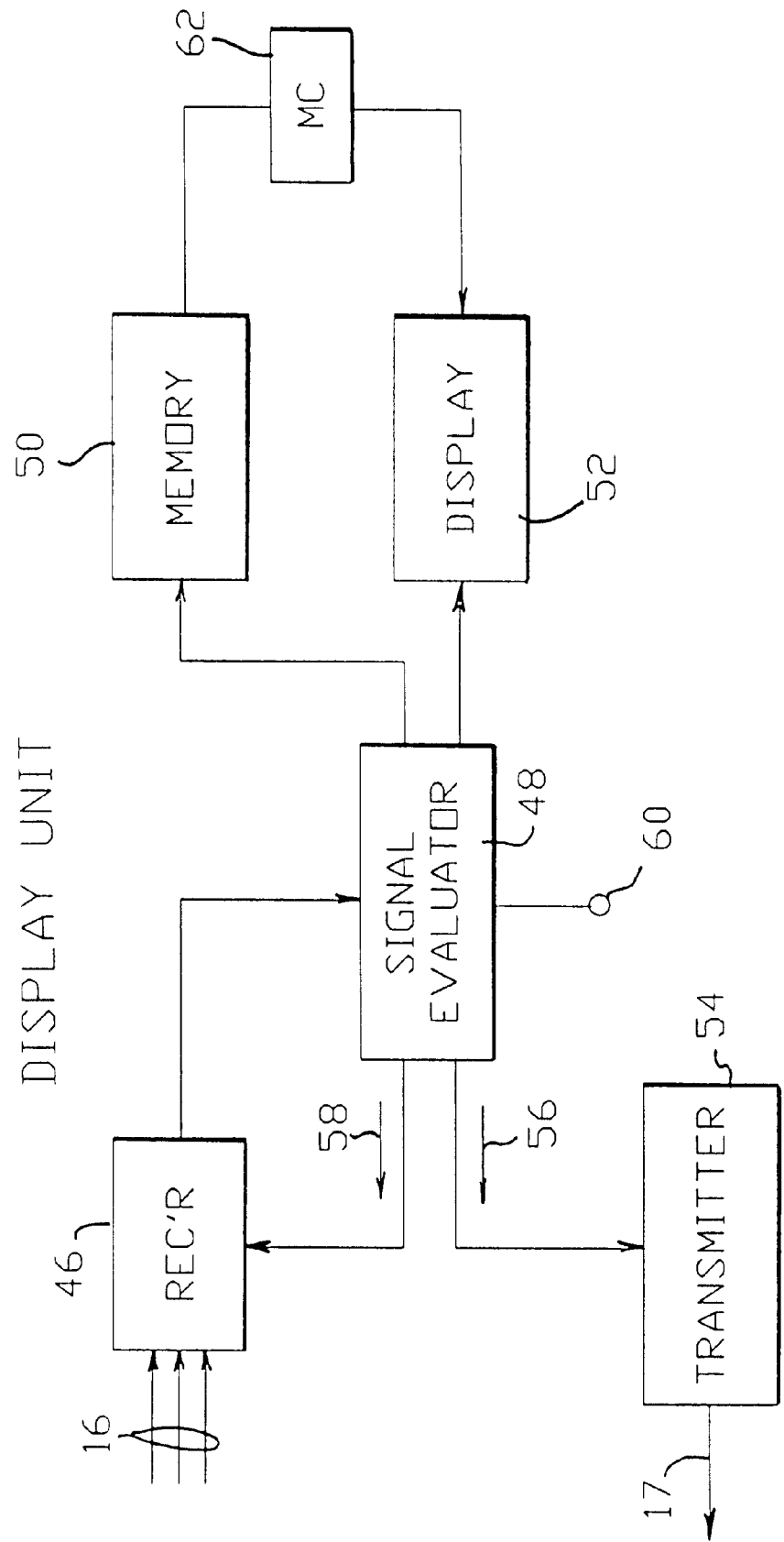
FIG. 5 is a schematic illustration of the wrist unit in more detail, showing the components comprising this unit.

Wrist Unit 14 (FIG. 5)

FIG. 5 illustrates the components which make up the wrist unit 14 (display). This unit provides the general functions of receiving the encoded digital signal representing a person's heartbeat, comparing the identification portion of the encoded signal to the appropriate reference identification pattern, and displaying and/or storing the data representing this heartbeat. Another function that is accomplished is a check of the data portion of the encoded signal to determine if any errors therein are within an acceptable bound or, if they are not, generating a signal to change the transmitter frequency as well as the frequency of the receiver in the wrist unit. As noted, this error detection and correction means takes into account transient errors which do not repeat and for which a frequency change is not required, as well as persistent errors which necessitate a change in transmission frequency in order to provide accurate data transmission. In this continuation-in-part application, the "wrist" unit is located in the exercise equipment and is used to control the part of the equipment which regulates the resistance offered to the user.

In more detail, wrist unit 14 contains a receiver 46 for receiving the encoded digital signals 16 from chest unit 12, a comparator or signal evaluator 48 for analyzing the received encoded signals, a memory unit 50 in which data representing heartbeat can be stored, a display unit 52 for displaying to the user his or her heartbeat, and a transmitter 54 for the wireless transmission of frequency change signals to the chest unit in order to change the frequency of transmission.

The electromagnetic signal 16 is received by receiver 46 and transformed into a digital signal that is sent to the comparator 48. This digital signal is identical to the outgoing digital signal transmitted from chest unit 12 to wrist unit 14. In the comparator 48, the received digital signal is separated into its identification part and its data part. The identification part of the signal is compared to the preset and unit-specific identification unique to this heartbeat monitor. If the identification part of the incoming signal does not match the reference identification part, the incoming signal is ignored. If there is a match, comparator 42 then checks whether the data portion of the incoming signal is in the proper pattern order shown for example, in FIG. 3B for a situation in which m=2. If the data bit sequence matches the reference sequence, then the transmission from the chest unit 12 to the wrist unit 14 was error free and the necessary signal evaluation can be done. This means that the information can be sent directly to display 52 and/or stored in memory 50.

If the data portion is not the expected pattern, the number of missing patterns is determined. This number also gives information about the severity of the transmission error. The necessary approximations to compensate for this error are then done in the signal evaluation unit 48 in order to compensate for the error. For example, if only one bit is missing from the expected pattern, the signal evaluator would have built-in logic that would provide the bit so that the heartbeat rate corresponding to that data pattern would be displayed. If the error is a major one but does not repeat itself, the signal evaluator will cause the last displayed heartbeat rate to remain displayed.

If the occurrence of transmission errors is beyond a given bound then the signal evaluator unit will automatically generate a frequency change signal 56. This signal will be sent to the transmitter 54 for wireless transmission (represented by arrow 17) to the receiving means 40 in chest unit 12 (FIG. 4). The selection of the new transmission frequency takes into account the recent history of transmission failures for the various frequencies. This can be done by a table look-up feature in signal evaluator 48 where the number of transmission errors is stored for each of the transmission frequencies. Signal evaluator 48 also provides a frequency change signal 58 to the receiver 46. This enables receiver 46 to have a receiving frequency matching that of the new frequency used in the transmitter 37 (FIG. 4).

As an alternative, the user can use input terminal 60, which is connected to the signal evaluator 48, in order to either block the change of frequency or to initiate a change in frequency.

Normally a change(s) in transmission frequency will provide accurate data to the receiving unit. However, if the monitor detects errors that continue to occur after several frequency changes, the internal logic in the monitor will prevent the further display of heartbeat rate (blank screen), and/or will provide an alarm signal. In this way, the user is not fooled by the display of an inaccurate heartbeat as occurs with presently available monitors.

The data evaluation leading to information for updating the display can be sent to the memory 50 besides being entered into the display 52. Later this stored data can be displayed in the display 52. Microprocessor 62 would control the flow of heartbeat data from memory 50 to display 52. Display 52 can be of the visual type such as an LCD display and/or can be audible, as for example an alarm or other sound representing a heartbeat count.

The transmitter-receiver pair 37-46 can communicate on several frequencies and uses a relatively low power signal in order to preserve battery life. The transmitter-receiver pair 54-40 communicates on only one frequency and uses a relatively high power signal, in a preferred embodiment. This takes into account that the transmitter-receiver pair 37-46 is in constant use and that hardware is provided for error detection and correction. In contrast, the transmitter-receiver pair 54-40 is only rarely used and the monitor 10 has no error detection/correction facility with respect to the encoded signal representing a frequency change selection.

The transmitter 54 will continue transmitting an electromagnetic signal 17 until a correct electromagnetic signal 16 is delivered by transmitter 37 to receiver 46 in the wrist unit. If for some reason this synchronization fails, the user can synchronize the chest and wrist units by external means.

Figure 6:
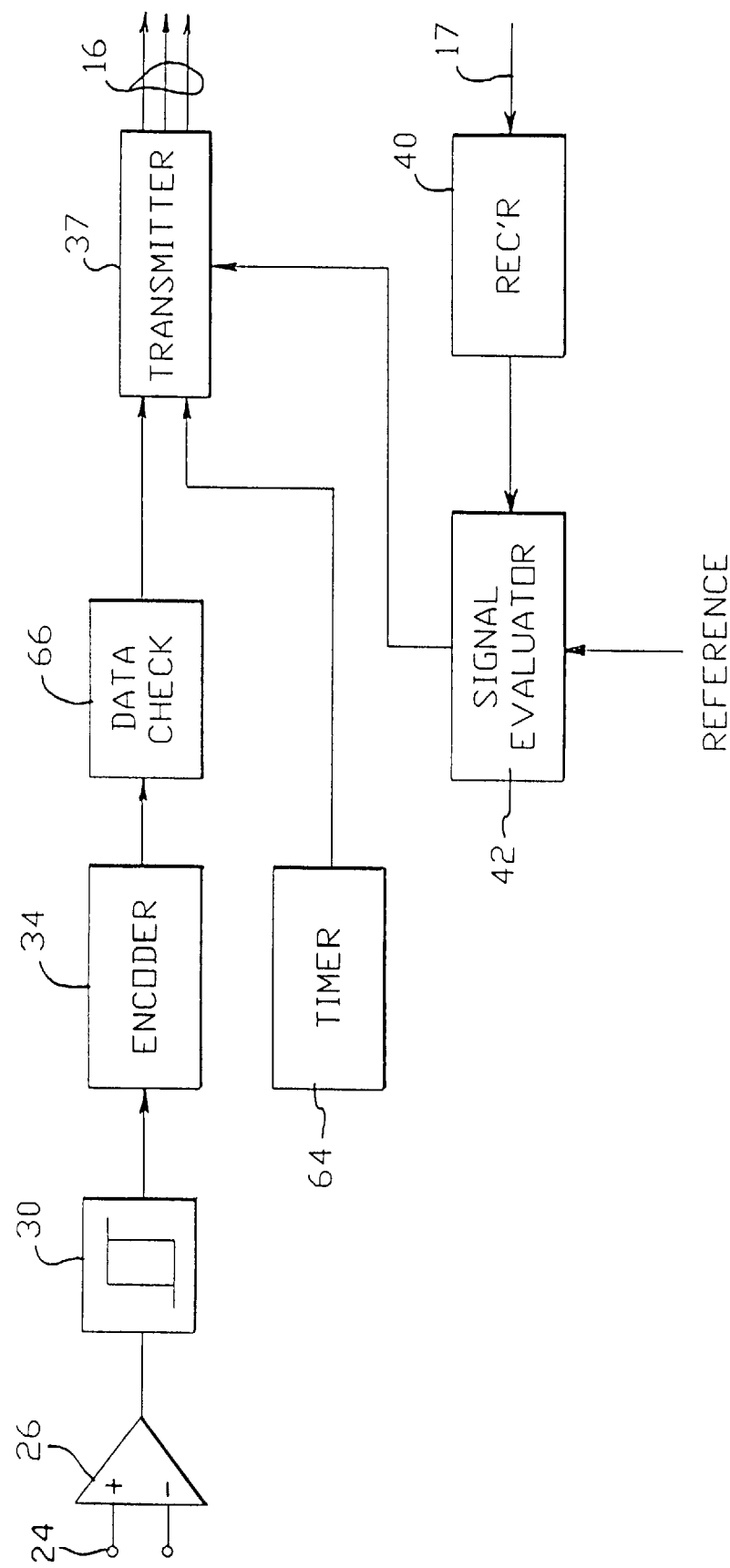
FIG. 6 is a schematic illustration of a modified chest unit, where the encoded digital signal represents the full heartbeat rate.

FIG. 6 illustrates a modification of the transmitter unit which is particularly adapted for wireless transmission of the full heartbeat rate. The same reference numerals will be used in this figure as were used in FIG. 4, for components having the same or similar functions. Of course, the unit of FIG. 4 can also be used to encode and transmit the full heartbeat rate.

In more detail, the transmitter of FIG. 6 includes the amplifier 26, comparator 30, encoder 34, transmitter 37, receiver 40 and signal evaluator 42 shown also in FIG. 4. However, a timer 64 is now used to trigger the transmitter 37 for wireless transmission of the encoded digital signal from encoder 34. In this embodiment, a data check circuit 66 is used to enable error detection and correction of the encoded digital signal prior to its being transmitted to the receiver unit. For example, this can be done by use of a parity bit. This helps to ensure accuracy is the entire heartbeat rate is to be transmitted, particularly if the heartbeat rate is not transmitted at a high repetition frequency, i.e., if there is a long time duration between each wireless transmission of heartbeat rate. The receiver unit of FIG. 5 can be used to receive and evaluate the full heartbeat rate sent by the transmitting unit.

Many different types of encoding can be used to represent the identification and data portions of the transmitted signals. Also, the rate of sampling of the ECG pulses can be varied, as can the repetition rate at which wireless transmissions of the encoded digital signal are made. The frequency change signal used to trigger a new transmission frequency can be transmitted over a multiple frequency range rather than over a single selected frequency. The frequency ranges used in the main transmission path can be chosen by the designer in accordance with known principles of wireless transmission, which in personal use monitors is of a short range.

As noted, the principles of digitization of the transmitted heartbeat signal transmission frequency changes, and signal encoding to ensure the accuracy of the communicated results are used to provide personal use monitors far superior to those presently being marketed. However, such principles may be applied to other than personal use monitors. It is recognized, though, that the provision of such features is unique in a wearable heartbeat monitor where the monitor includes a wearable transmitting unit and an associated display unit. These features are also unique to monitors where the display (receiver) unit is located on exercise equipment or is a small unit that can be placed in a suitable location for viewing by the user. Such units are distinguishable from large hospital units wherein a central computer is used to coordinate a multiplicity of transmitting and/or display units.

While the monitor has been illustrated in an embodiment thereof for monitoring heartbeat rate, it will be understood by those of skill in the art that a signal indicative of another physical condition can be monitored. For example, an acoustical sensor can detect a pulse or a thermometer sensor can detect a temperature. This type of monitor can be applied to measure and display any type of life function, in persons or animals. Additionally, wireless monitors for measuring physical conditions other than life functions can utilize the principles of error detection and correction described herein.

While it has been mentioned that the display (receiver) unit can be located on exercise equipment, the monitor can be used for controlling intensity and type of workout on exercise equipment based on continuously monitoring a body response of the target person. For example, the exercise equipment can be programmed to receive a continuous heart rate response of the target person and then adjust the intensity (such as resistance) of the exercise to maintain the person's heart rate within a preselected range.

The monitor of this invention is particularly suitable for use with exercise equipment since it is insensitive to the closeness of other exercise equipment, motors within the equipment being used by the person, and other closely located monitors operating on the same or close frequency ranges. This allows the receiver-display unit to be located anywhere on the exercise equipment without concern for interference effects which would yield the wrong heart rate and correspondingly provide an incorrect workout.

It is well known that exercising in a correct amount plays an essential role in any effort to fight cardiovascular disease and certain forms of cancer. However, the best result can only be achieved when the correct way of exercising is selected. In the past, this has led to certain rules of thumb such as exercising at 70% of the maximum heart rate, where the maximum heart rate is given by the expression (220 minus age). In order to obtain this, a constant monitoring of the heart rate during exercise is required and there must ben a adaptation of the intensity level of the exercise based upon the heart rate. As the heart rate of a person depends on a variety of daily factors such as sleep, diet, health etc., it is not sufficient to determine the best type and intensity of exercise for a person only one time, e.g., in a doctor's office, and then stay with this level over a long period of time. Additionally, the training effect of exercise itself leads to a gradual shift in the exercise level which is best suited for the individual.

Until only recently, the control of the intensity level of the exercise equipment was left completely in the exercising person. Even when the person had an accurate heart monitor he/she still had to adjust the intensity of the exercise according to the reading on the monitor. Only in closely supervised programs such as those undertaken by professional athletes or persons in a cardiac rehabilitation program was this task taken over by a trainer or a doctor.

Since exercise equipment is now used in many forms of exercise activities, it is appropriate to incorporate some means of exercise level control into the equipment. A first step has been done by some companies which offer exercise bikes allowing the constant measurement of heart rate as long as the exercising person touches two electrodes with his/her hands. The measured heart rate is then used by the bike control circuit to increase or reduce the resistance of the bike in order to keep the heart rate of the target person within a selected range.

Although this type of exercise bike is certainly a step in the correct direction, this equipment has several significant disadvantages. While it may be somewhat inconvenient, a target person can probably be convinced to keep a firm grip on the handles of the exercise bike. However, this technique cannot be used for other kinds of exercise equipment such as treadmills or stairclimbers, where a constant contact of the skin with electrodes on the equipment cannot be guaranteed. It is also doubtful that this technique can be generalized to be used for measuring other body responses, such as blood pressure. Further, this type of heart monitoring does not allow for warm-up and cool-down phases which are essential in the design of proper exercise. In some cases, doctors will even suggest that for persons with limited available time that the exercise should consist only of a warm-up and cool-down phase. In such an event, the aforementioned exercise bike will not provide the proper workout.

As the heart rate is supposed to change during the phases of warm-up, aerobic workout, and cool-down, a more complex control mechanism is necessary than for a phase in which a constant target heart rate is sought. Further, in an exercise bike, like in many other exercise equipments, there are often multiple parameters which determine the intensity of the exercise. For the exercise bike, these parameters are the pedal speed and the resistance. In presently available exercise bikes, only the resistance is controlled by the heart rate. Still further, these exercise bikes cannot keep track of the exercise history of the target person and take this into account in deriving the best exercise type and level. Although the heart rate has a very short response time to a change in exercise intensity, this may not be the case for other body responses. If there is a significant delay between a change in the exercise intensity and a corresponding change of the body response, this must be anticipated by a more complex control algorithm; that is, the exercise equipment control should not be restricted to a feed-back type regulation but should also incorporate a feed-forward control in which the equipment parameters are adjusted ahead of time in order to eliminate excess overshoots and undershoots of the measured body response.

There are also some exercise bikes being marketed which use wireless monitors to measure heart rate of the exercising person and to use that heart rate to adjust the exercise work load. In some instances, different exercise programs can be incorporated into the equipment, where these programs have predetermined resistance levels to simulate hills or flat terrain.

FIG. 7 schematically illustrates the use of the present monitor with exercise equipment, in this case an exercise bike. The transmitter unit of the monitor is located on the person while the receiver unit is located on the exercise equipment. The receiver includes a display which indicates the biomedical response, such as heart rate, and also provides an electrical signal for controlling one or more exercise parameters, such as pedal rate and resistance. In FIG. 7, the transmitter unit 12 provides a digitally encoded signal 16 in a wireless manner to the receiver 14, which is coupled to the display and controller in the exercise bike 70.

The use of a wireless transmission ensures that the user will not be constrained in his freedom of body movement regardless of the type of exercise equipment that is employed. The features of error detection and error correction, together with the means for changing transmission frequency allow accurate heart rates to be transmitted even in rooms which are crowded with exercise equipment or with numerous people wearing heart rate monitors.

It is desirable that the exercise profile of the present exercise be derived from an input from the user. An already stored history of this specific user and the baseline of the user's body response will provide more appropriate exercise. Of course, the user can also override this feature and enter his own profile. In this invention, the whole exercise profile including the warm-up and cool down and any other interval portions are continuously adjusted depending upon the measurement of the body response.

The receiver-controller unit on the exercise equipment is operated in response to the measured biomedical function, such as heart rate. As different parameters of the exercise equipment may employ different muscle groups, the composition of the parameter selection will depend on the exercise history of the target person. For example, both arms and legs may be subject to different exercises, each of which will affect heart rate.

For each exercise urn, key characteristics of this run will be stored in memory and used to refine the exercise profile of the same person. Since this requires a technique to distinguish between different persons using the exercise equipment, identifiers are used as are used with the digitally encoded signal (i.e., the identification portion).

A microprocessor in the exercise equipment will take into account the present and previous heart rates of the person and make these rates subject to a weight function in order to give the most consideration to most recent heart rate, but not to disregard the previous heart rates. For instance, the same present heart rate must result in different actions if it is a sudden increase over the previous heart rates or if it is the same as the previous heart rate or even a decline in heart rate. After the exercise run, the key characteristics of the run are extracted and stored in a memory of the equipment to be available for future exercise activity of the same person.

FIG. 8 shows the various components of the receiver-controller unit. This unit can include the various components shown on FIG. 5, where FIG. 8 shows the receiving means 46 for receiving the digitally encoded signal 16 from the transmitting unit 12. Although it is not shown in FIG. 8, the receiver/controller unit would include the transmitter 54 (FIG. 5) used to change frequency if there is excess interference. The functions of the other components (signal evaluator 48, memory 50, display 52, input terminal 60, and microprocessor 62 of FIG. 5) are provided by the components shown in FIG. 8.

Microprocessor 72 is a major component of the receiver-controller and provides the logic, signal recognition and identification, and instructions to the exercise parameter control unit 74 for controlling the exercise intensity in accordance with a desired exercise profile based on the target person, the type of exercise to be undertaken, and the time period for the exercise.

A magnetic strip reader 76 is used as an identification means in order to identify the target person. Other forms of identification could also be used, including a keyboard entry of a coded identifier. The purpose of this component is to identify the exercising person to the equipment so that the receiver in the receiver-control unit will be synchronized with the transmitting unit assigned to that user. Further, the use of an input device, such as a magnetic strip card which can be read by reader 76, enables a person to lead his or her personal data into an internal memory 78 so that a proper profile can be assigned by microprocessor 72. It may be that the internal memory 78 already has stored information relative to that user which can be directly implemented by the microprocessor 72 in establishing the exercise parameter control unit 74 for a particular resistance, pedal speed, evaluation, etc. depending upon the type of exercise equipment to be used (exercise bike, stairclimber, etc.).

A console input 80, such as a keyboard mechanism or remote control, is also electrically connected to the microprocessor 72. The console input unit 80 allows the user to manually control the exercise parameters he/she wishes to employ, thereby overriding the profile control that the microprocessor 72 would normally adopt. Console input 80 allows the user to deviate from programmed control of the exercise equipment at any time depending on personal needs and desires.

Console display 82 receives inputs from microprocessor 72 and displays the person's heart rate. Displays are also for indicating exercise parameters such as pedal speed, resistance, elevation, etc., as well as time, height, weight, age etc. In a normal program, one third of the complete exercise time would be used for warm-up and one third would be use for cool down. The remaining one third would be used to provide an exercise regimen at the desired heart rate, which could, for example, be at an aerobic rate (about 70% of the desired maximum heart rate for that individual.

Internal memory unit 78 contains stored programs for the operation of the microprocessor, including those programs which enable it to analyze the incoming digitally encoded signal in order to read the identification part, error correction part, and hearty rate data portion, as described previously. Memory 78 also provides storage of data of the user at that time, including the user's previous workout data. The advantage of internal memory 78 is that it enables the receiver-controller unit to recognize the past performance of a person in order to better control fluctuations that might be seen when a new exercise program starts. In this manner, the microprocessor 72 will not call for radical changes of the exercise parameter control 74 due to nonsignificant changes in heart rate. For example, it may be that a person's heart rate jumps to a high level very quickly in the warm-up phase of exercise, and thereafter stabilizes. Having this data in internal memory 78 prevents the microprocessor from radically decreasing the resistance, etc. of the exercise equipment which would not provide the proper warm-up for this type of person. Of course, the user can override any preprogrammed profile by using the console input 80.

An external memory unit 84, using for example a magnetic or optical disk, provides a universal say for allowing any piece of exercise equipment to be used by any individual. For example, a person can take his/her disk to any gym and enter a desired profile using the external memory unit 84 which interacts with the microprocessor 72. When this is done, there will be an override of any profile program from internal memory 78, or the user can elect to use a default program stored in internal memory 78.

The following will now detail the use of exercise equipment operated under control of the receiver-controller unit of FIG. 8, where the biomedical response is illustratively a heart rate as measured and wirelessly transmitted using the monitor of this invention. In operation, the user first identifies himself at the console of the exercise equipment prior to the exercise, e.g., by entering a password or by using the magnetic strip reader 76. If there already exists an exercise history file for this user, the user is asked to enter some information about the exercise which he/she plans to do. This information is entered using the console input unit 80 and may include the planned exercise time and the type of exercise, such as interval training or cardiovascular workout. The user can also override the automatic profile generation stored in the internal memory 78 by entering his/her own intensity or heart rate profile. This can be done, for example, by inserting the user's disk in the external memory reader 84. If there is no exercise history file for the user in internal memory 78 and no stored data is entered using unit 84, the user is asked to enter various personal data such as age, weight, height, gender etc. These data will then be stored in the exercise history file of the user in internal memory 78, and will be used for his/her future exercises. The user then receives various default profiles from which to choose. These profiles will include a warm-up time, a cool-down period and a period of time in which an aerobic heart rate will be maintained.

The user then attaches the heart rate monitor to the appropriate body part, usually the chest, and takes the desired position on the exercise equipment without starting exercising. The microprocessor 72 controls whether a heart rate is obtained and whether the transmission is reliable, that is, whether the heart rate is not fluctuating in a large range or is outside the expected range. If anything unusual is registered, the user is asked to take corrective action, such as moistening the electrodes of the transmitter unit. The user can also override this feature if he/she is convinced that everything is fine and if the user knows that his/her heart rate is usually high or low.

After this, the user is asked to start exercising. The first short time frame of low intensity exercise is used for the microprocessor 72 to establish a baseline for the user. This baseline reflects the present state of the user and thus considers momentary health, possible lack of sleep, diet etc. Based on this baseline and one the selected exercise profile, microprocessor 72 makes a preliminary assignment of exercise parameters to time points during the exercise run and the expected heart rate.

After these preliminaries, the user starts his/her exercise. The heart rate is continuously monitored and transmitted to the receiver 46 in the exercise equipment. Receiver 46 transfers the data to the microprocessor 72 where the integrity of the data is checked. If the data passes this integrity check, meaning that no error has been detected, the measured heart rate is used to adjust the exercise intensity level based on the deviation of the measured heart rate from the projected heart rate. If the exercise equipment has several parameters to be set, for example pedal rpm and resistance in an exercise bike, the user receives a proposed value for a parameter that he/she can control. For example, the user can set the pedal rpm at 80 rpm while the other parameter (resistance) is adjusted by the receiver-controller in accordance with the continuously monitored heart rate. If it can be detected that the user cannot maintain the suggested parameter, the proposed parameter is modified. For example, the proposed pedal rpm value can be reduced to 70. If microcomputer 72 detects a sequence of errors in the received data, it notifies the user via the console display 83 that it cannot any longer control the run based on the measured heart rate. Microprocessor 72 then gives the user the choice to continue the exercise run without this control or to gradually stop the exercise. This operation runs under control of instructions received from internal memory 78. If the heart monitor senses recurrent errors beyond that which can be corrected by the error detection and correction means, a frequency change is used to determine another frequency in which correct wireless transmission of the correct heart rate will be obtained.

After the exercise run, microprocessor 72 will extract the key characteristics of the exercise, such as maximum heart rate after a specified exercise time, the relevant intensity level, warm-up and cool-down times, and baseline values at the beginning and at the end of the exercise run. These key characteristics will be stored in internal memory in the exercise history file for the specific user. They can also be written into an external memory disk placed in the receiver-controller external memory unit 84.

In contrast with existing equipment, the apparatus shown in FIGS. 7 and 8 uses a microprocessor and associated memories to store background information indicative of a particular person, and uses identification means to tailor an exercise run to a user's specific profile. Further, this equipment is based on an instantaneous heart rate measurement at all times, not just on a single set heart rate or on preprogrammed times for setting various exercise levels. Because the monitor of this invention provides error detection and correction, and because it has the capability of changing frequency in order to eliminate interference effects, it can be used on all types of exercise equipment and in the presence of many users in the same exercise room. That is, the proximity of many users wearing heart monitors and closely spaced motor-driven exercise equipment will not lead to errors. This is particularly important where the exercise run is being controlled throughout its time duration in accordance with a continuously monitored heart rate. Thus, the use of the monitor of this invention to provide continuous control exercise equipment offers several unique features and advantages.

While this invention has been described with respect to particular embodiments thereof it will be apparent to those of skill in the art that variations may be made without departing from the spirit and scope of the present invention, which is to be measured only by the appended claims. Body responses other than heart rate, such as temperature, blood pressure etc. can also be used to automatically control exercise using this monitor.

I claim:

1. A monitor for determining and displaying a biomedical condition including:

sensor means for sensing a biomedical condition and producing an output, a transmitting means including means for producing a first identification signal identifying said transmitting means and means for using said sensor output to produce a second signal used to determine a biomedical condition, said transmitting means including a transmitter for wirelessly and repeatedly transmitting said first and second signals to a receiver over a first frequency, a receiver for receiving said first identification signal and said second signal, as well as interfering signals, if any, identification means using said received first identification signal to determine if said second signal is from said transmitting means thereby overcoming the effect of said interfering signals, means for rejecting said second signal if it is not from said transmitting means, means using said second signal to determine said biomedical condition, and a display means for displaying said biomedical condition if said second signal is from said transmitting means.

2. The monitor of claim 1, further including encoding means for digitally encoding said first and second signals.

3. The monitor of claim 1, further including an encoder for digitally encoding said first signal.

4. The monitor of claim 1, further including means for producing a reference signal and means for comparing said second signal received by said receiver to a reference signal to determine if transmission errors have occurred in said second signal.

5. The monitor of claim 4, further including correction means for correcting said errors.

6. The monitor of claim 4, further including means in said transmitter for setting the frequency over which said wireless transmission occurs and means for changing the frequency over which said wireless transmission occurs from said first frequency to a second frequency, said receiver including means enabling the receiver to receive wireless transmission at said second frequency.

7. The monitor of claim 1, further including correction means for correcting errors in said second signal used to determine said biomedical condition.

8. A method for monitoring the heartbeat rate of a person comprising the steps of:

using a sensor to obtain an output based on a biomedical condition of said person, said output being related to the heartbeat rate of said person, producing a first signal used to determine heartbeat rate from said sensor output, repeatedly wirelessly transmitting said first signal over a first frequency from a transmitter to a receiver, determining the heartbeat rate, changing the frequency over which said first signal is wirelessly sent from said transmitter to said receiver, to a second frequency adapting the receiver to receive wireless transmission from said transmitter at said second frequency, and displaying said heartbeat rate.

9. The method of claim 8, including the further step of providing an identification signal representing said transmitter, and repeatedly wirelessly transmitting said identification signal from said transmitter to said receiver, wherein said heartbeat rate is displayed only if said identification signal is received by said receiver.

10. The method of claim 9, including the further step of encoding said identification signal.

11. The method of claim 10, where said identification signal is digitally encoded.

12. The method of claim 9, including the step of encoding said first signal.

13. A method for monitoring the heartbeat rate of a person comprising the steps of:

using a sensor to obtain an output based on a biomedical condition of a person, said biomedical condition containing heartbeat information, using said sensor output to produce a first signal used to determine heartbeat rate, repeatedly wirelessly transmitting said first signal over a first frequency from a transmitter to a receiver, producing an identification signal identifying said transmitter even in the presence of interfering signals, repeatedly wirelessly transmitting said identification signal from said transmitter to said receiver, determining said heartbeat rate using said first signal, and displaying said heartbeat rate only if said identification signal identifies said transmitter.

14. The method of claim 13, including the step of encoding said identification signal.

15. The method of claim 14, where said encoding step is a digital encoding step.

16. The method of claim 13, including the step of encoding said first signal.

17. The method of claim 13, including the further steps of detecting if said first signal deviates from an expected pattern and recovering from said deviation if present in said received first signal to produce a signal representing heartbeat rate.

18. The method of claim 13, including the further steps of detecting an error in said first signal and correcting said first signal.

19. A personal heartbeat monitor comprising:
   sensor means for providing an output responsive to a biomedical condition, said biomedical condition containing heartbeat information,
   means for producing a first signal from the output of said sensor means, said first signal being usable to determine heartbeat rate,
   a transmitter for repeatedly wirelessly transmitting said first signal from said transmitter to a receiver,
   a receiver for receiving said first signal that is wirelessly transmitted from said transmitter,
   means for determining heartbeat rate using said first signal,
   means enabling the frequency over which said repeated wireless transmission of said first signal occurs to be changed,
   means enabling said receiver to match the frequency change of said transmitter, and
   display means for displaying heartbeat rate.

20. The monitor of claim 19, including means for producing an identification signal associated with said transmitter, means for repeatedly wirelessly transmitting said identification signal from said transmitter to said receiver, means in said receiver for using said identification signal to determine if said first signal is from said transmitter and means for enabling said heartbeat rate to be displayed if said first signal is from said transmitter.

21. The monitor of claim 20 including means for encoding said identification signal.

22. The monitor of claim 19, where said receiver is sufficiently small to be hand-held by a person using said personal heartbeat rate monitor.

23. A biomedical condition monitor, comprising:
   a sensor for producing an output based on a biomedical condition,
   an encoder for producing an encoded digital signal from said output,
   a transmitting unit for repeated wireless transmission of said encoded digital signal to a receiver,
   a receiving for receiving said wirelessly transmitted encoded digital signal,
   means for receiving and using said encoded digital signal to produce a signal representative of said biomedical condition,
   correcting means for correcting errors in said signal representative of said biomedical condition, and
   a display for displaying said biomedical condition.

24. The monitor of claim 20, where said biomedical condition is heartbeat rate.

25. The monitor of claim 23, further including means in said transmitter for producing electromagnetic pulses for identifying said transmitter and an identification circuit that receives said electromagnetic pulses for determining if said wirelessly transmitted encoded digital signal is from said transmitting unit.

26. The monitor of claim 23, further including a frequency circuit for enabling a change in the frequency over which said wireless transmission occurs if interference in said transmission occurs.

27. A personal heart rate monitor, including
   a transmitting means for producing an encoded signal representative of a person's heart rate, said transmitting means including sensor means for producing a signal representative of a person's heart rate, said transmitter means containing a transmitter for repeated wireless transmission of said encoded signal to a receiving means, and
   a receiving means for receiving said repeated wireless transmission of said encoded signal, means for determining if said received encoded signal is from said transmitting means, means for detecting errors in the received encoded signal, correcting means for presenting to a display a signal representing heart rate that corrects for said errors, and a display for displaying said heart rate.

28. The personal monitor of claim 27, where said correction means includes means for changing the frequency over which said encoded signal is transmitted, said frequency changing reducing the likelihood of errors in said wireless transmission.

29. The personal monitor of claim 27, where said means for determining if said received encoded signal is from said transmitting means includes means for generating a series of electromagnetic pulses used to discriminate transmission of said encoded signal from said transmitting means from any other transmission.

30. The personal monitor of claim 29, where said series of electromagnetic pulses is unique to the transmitting means and receiving means.

31. A method for personal monitoring of a biomedical condition, including the steps of
   using a sensor to produce an output representative of said biomedical condition,
   producing an encoded signal representative of a biomedical condition from said sensor output,
   repeatedly wirelessly transmitting said encoded signal from a transmitter to a receiver,
   receiving said encoded signal in said receiver,
   determining if said encoded signal received by said receiver is from said transmitter,
   rejecting said encoded signal if it is not from said transmitter,
   detecting if said received encoded signal deviates from an expected pattern of said encoded signal,
   recovering from said deviation if present in said received encoded signal to produce a signal representing said biomedical condition for display, and
   displaying said biomedical condition if said encoded signal is from said transmitter.

32. The method of claim 31, where the steps of determining if said encoded signal received by said receiver is from said transmitter includes the steps of producing a series of pulses that identify said transmitter to said receiver, repeatedly wirelessly transmitting said series of pulses from said transmitter to said receiver, and reading said series of pulses to determine if said encoded signal in said receiver is from said transmitter.

33. The method of claim 32, including the step of determining the magnitude of said biomedical condition using the output of said sensor, and wirelessly transmitting a signal representing said magnitude from said transmitter to said receiver.

34. A personal monitor for monitoring a biomedical condition, including sensor means for producing an output used to determine said biomedical condition, said output being sent to an encoder, an encoder for producing an encoded signal used to determine said biomedical condition, a transmitter for repeated wireless transmission of said encoded signal to a receiver, said wireless transmission being subject to interference from sources of electromagnetic energy other than said transmitter, a receiver for receiving said encoded signal from said transmitter, means for determining the value of said biomedical condition from said sensor output, means for determining in the presence of interference, if said encoded signal received in said receiver is from said transmitter, means for rejecting said encoded signal if it is not from said transmitter, means for detecting errors in said received encoded signal, means for correcting said errors, and means for displaying said biomedical condition.

35. The personal monitor of claim 34, where said means for determining the value of said biomedical condition produces an output that is sent to said encoder, said encoder producing an encoded signal representing the value of said biomedical condition, said encoded signal being repeatedly wirelessly transmitted to said receiver.

36. The personal monitor of claim 35, where said encoder is a digital encoder.

37. The personal monitor of claim 35, where said biomedical condition is heartbeat rate.

38. A personal heart rate monitor, including a sensor for producing an output used to determine heart rate, means using the output of said sensor for producing a heart rate signal representing heart rate, an encoder for encoding said heart rate signal to produce an encoded heart rate signal, a transmitter for wirelessly transmitting said encoded heart rate signal to a receiver, a receiver for receiving said encoded heart rate signal from said transmitter, identification means for determining if said received encoded heart rate signal is from said transmitter, means for detecting errors in said received encoded heart rate signal, means for correcting said errors, and means for using said received encoded heart rate signal for displaying said heart rate.

39. The personal monitor of claim 38, where said encoder produces a series of pulses that represent heart rate and provide an identification code that is read by said identification means to determine if said received encoded signal is from said transmitter.

40. The personal monitor of claim 39, where said encoder includes means for digitally encoding said heart rate signal.

41. A biomedical condition personal monitor, including:

a wearable transmitting means for producing an encoded digital signal representative of a person's biomedical condition, said transmitting means including sensor means for producing an electrical signal representative of said biomedical condition, said transmitter means containing a transmitter for wireless transmission of said encoded digital signal to a display means and a display means for producing a display of said person's biomedical condition, said display means including a receiver for receiving said wireless transmission of said encoded digital signal, means for determining if said received encoded signal is from said transmitting unit, means for detecting errors in the received encoded digital signal and means for correcting said errors in said wireless transmission.

42. The monitor of claim 41, where said transmitting means includes means for encoding said electrical signal representative of a person's biomedical condition to produce said encoded digital signal, said signal including a first part identifying said monitor and a second part which represents the biomedical condition of said person.

43. The monitor of claim 42, wherein said means for determining includes means for comparing said received encoded digital signal with a reference signal produced by said display means to determine if said received encoded digital signal has been sent from said transmitting means.

44. A personal monitor, including:

a means for producing an encoded signal representative of a biomedical condition related to a person's heartbeat, a transmitter for wireless transmission of said encoded signal to a receiver, a receiver for receiving said wireless transmission of said encoded signal, an identification device for determining if said received encoded signal is from said transmitter, a detector for detecting errors in the received encoded signal, a correcting device for correcting said errors in said wireless transmission, and a display for indicating said biomedical condition.

45. The monitor of claim 44, including an encoder for producing an encoded digital signal, said encoded digital signal including a first part for identifying said monitor and a second part which can be used to determine said biomedical condition.

\* \* \* \* \*